United States Patent [19]

Ogura et al.

[11] Patent Number: 4,581,942
[45] Date of Patent: Apr. 15, 1986

[54] MEASURING CONDUIT FOR FLOW RATE AND CONCENTRATION OF FLUID

[75] Inventors: Ichiro Ogura, Yokohama; Kaoru Machida, Ootawara; Muneshige Kurahashi, Tokorozawa, all of Japan

[73] Assignees: Kabushiki Kaisha Toshiba, Kawasaki; Nihon Kohden Corporation, Tokyo, both of Japan

[21] Appl. No.: 675,231

[22] Filed: Nov. 27, 1984

[30] Foreign Application Priority Data

Nov. 30, 1983 [JP] Japan ............................ 58-226131

[51] Int. Cl.$^4$ ........................... G01F 1/66; G01F 1/74
[52] U.S. Cl. ............................ 73/861.04; 73/861.28; 128/719
[58] Field of Search .................. 128/716, 719, 225; 73/861.04, 861.27, 861.28, 861.29

[56] References Cited

U.S. PATENT DOCUMENTS

| | | | |
|---|---|---|---|
| 3,901,078 | 8/1975 | McShane | 73/861.29 X |
| 3,906,791 | 9/1975 | Lynnworth | 73/861.29 |
| 4,425,805 | 1/1984 | Ogura . | |
| 4,522,204 | 6/1985 | Kurahashi et al. | 128/719 |

*Primary Examiner*—Herbert Goldstein

*Attorney, Agent, or Firm*—Oblon, Fisher, Spivak, McClelland & Maier

[57] ABSTRACT

A measuring conduit adapted for flow rate and concentration of a fluid for use in a measuring apparatus which measures both the flow rate of the fluid such as a respiratory gas containing a particular gas component, for example, carbon dioxide, using an ultrasonic wave and the concentration of the particular gas component in an optical manner. In order to simultaneously measure the flow rate and concentration and also to reduce the dead space of the measuring conduit, this measuring conduit comprises a single conduit member through which the fluid flows; a pair of ultrasonic transducers attached to the conduit member so as to face each other along a line slanted with respect to a flow direction of the fluid; and a pair of light transmitting windows airtightly provided in the wall of the conduit member between the ultrasonic transducers so as to face each other. One of the light transmitting windows introduces a light beam from an external light source into the conduit member. The other light transmitting window introduces the light penetrating the fluid flowing through the conduit member into a photo detecting element of the measuring apparatus.

4 Claims, 4 Drawing Figures

MEASURING CONDUIT FOR FLOW RATE AND CONCENTRATION OF FLUID

BACKGROUND OF THE INVENTION

The present invention relates to a measuring conduit which is used to simultaneously measure the flow rate of a fluid such as a respiratory gas and the concentration of a particular component in the fluid.

In the case of a fluid containing various kinds of components, there is often a demand for the measurement of the flow rate of a particular component. For example, when air or gas in which oxygen is artifically added to the air, such as a respiratory gas, is inhaled and the gas containing carbon dioxide is exhaled, the flow rate of carbon dioxide in the expiratory gas is used as carbon dioxide production for the evaluation of a respiration function.

A method which has been conventionally performed to measure carbon dioxide production is called the Douglas bag method. According to this method, an expired gas is collected into an airtight bag, and the product of its volume v and the carbon dioxide concentration $F_{CO2}$ is obtained. Finally, carbon dioxide production is determined by the average value during measuring period.

Due to the recent advancement in methods for measuring the flow rate of a fluid and for analyzing a component, the real-time measurement of the flow rate of the component has been made possible. For instance, to measure carbon dioxide production $V_{CO2}(t)$, the instantaneous flow rate $v(t)$ of expired gas and the instantaneous concentration of carbon dioxide $F_{CO2}(t)$ are simultaneously measured, and carbon dioxide production $V_{CO2}(t)$ is computed in the form of:

$$V_{CO2}(t) = v(t) \cdot F_{CO2}(t).$$

The flow-rate measurement and the concentration measurement are each performed while a fluid is flowing through a measuring conduit. To measure the flow rate and the concentration at a time, therefore, a measuring conduit for measuring the flow rate and a measuring conduit for measuring the concentration must be coupled in tandem. However, such a coupling of two measuring conduits makes the dead space in the respiration circuit fairly large. The resultant dead space equals the sum of the capacities of the measuring conduits. This puts a great burden on the respiratory organ of an examinee, causing difficulty in the examination of a serious patient.

In addition, the tandem coupling of the measuring conduits also causes a problem of measurement accuracy. A reason for such a problem is that both measuring times are slightly different due to the distance between two measuring points. Namely, assuming that the distance from the flow-rate measuring point to the concentration measuring point is L and a flow velocity of the fluid is V, the time $t_d$ (time difference) required for a lump of fluid undergoing the flow-rate measurement to reach the concentration measuring point is given by:

$$t_d = L/V.$$

From this it is evident that the time $t_d$ changes depending on the flow velocity. In order to eliminate the influence of this time difference $t_d$, the carbon dioxide production has been conventionally found as follows:

$$V_{CO2}(t) = v(t) \cdot F_{CO2}(t - t_d).$$

However, particularly in the case of a compressive fluid such as a respiratory gas, the flow velocity variously changes in one respiration, and a change in flow velocity is also caused due to a change in the pressure of such fluid. Therefore, the time difference $t_d$ complicatedly varies, and it becomes extremely difficult to strictly perform the correction as shown in the above equation.

SUMMARY OF THE INVENTION

It is an object of the present invention to provide a measuring conduit which enables the simultaneous measurements of the flow rate of a fluid containing a measured component and the concentration of the component.

Another object of the invention is to provide a measuring conduit adapted to measure the flow rate of a respiratory gas and the concentration of a gas component in the respiratory gas with as little as possible dead space in order to lighten the burden of a patient.

Still another object of the invention is to provide a measuring conduit adapted to measure the flow rate of a respiratory gas and the concentration of a gas component in the respiratory gas without causing a substantial time difference between the measurements.

The present invention is applied to a measuring conduit which is adapted to measure the flow rate of a fluid in an ultrasonic measuring manner, and the concentration of a particular gas component in the fluid in an optical measuring manner. The measuring conduit of the present invention comprises a single conduit through which a fluid flows; two ultrasonic transducers for measuring the flow rate of the fluid which are attached to the conduit so as to face each other along a line slanted with respect to the flow direction of the fluid; and a pair of light transmitting windows which are airtightly provided in walls of the conduit positioned between the ultrasonic transducers so as to face each other. One of the light transmitting windows introduces light from an external light source into the conduit, and the light transmitted through the fluid flowing through the conduit goes through the other light transmitting window and into a photo detecting element in an external concentration measuring apparatus.

Preferably, the two ultrasonic transducers and the two light transmitting windows are arranged so that the crossing point of the central line of the axis of the conduit and the central line of the ultrasonic beam which is transmitted and received between the ultrasonic transducers coincides with the central line of the light beam which passes through the pair of light transmitting windows.

According to the present invention, the flow rate and concentration measurements are performed at substantially the same locations in the conduit; in other words, they are performed almost simultaneously. Therefore, a time difference between the flow rate measurement and the concentration measurement can be minimized. Further, since the flow rate and the concentration can be measured by use of a single conduit with little dead space, the burden for a patient is remarkably reduced.

DESCRIPTION OF THE PREFERRED EMBODIMENT

Figure 1:
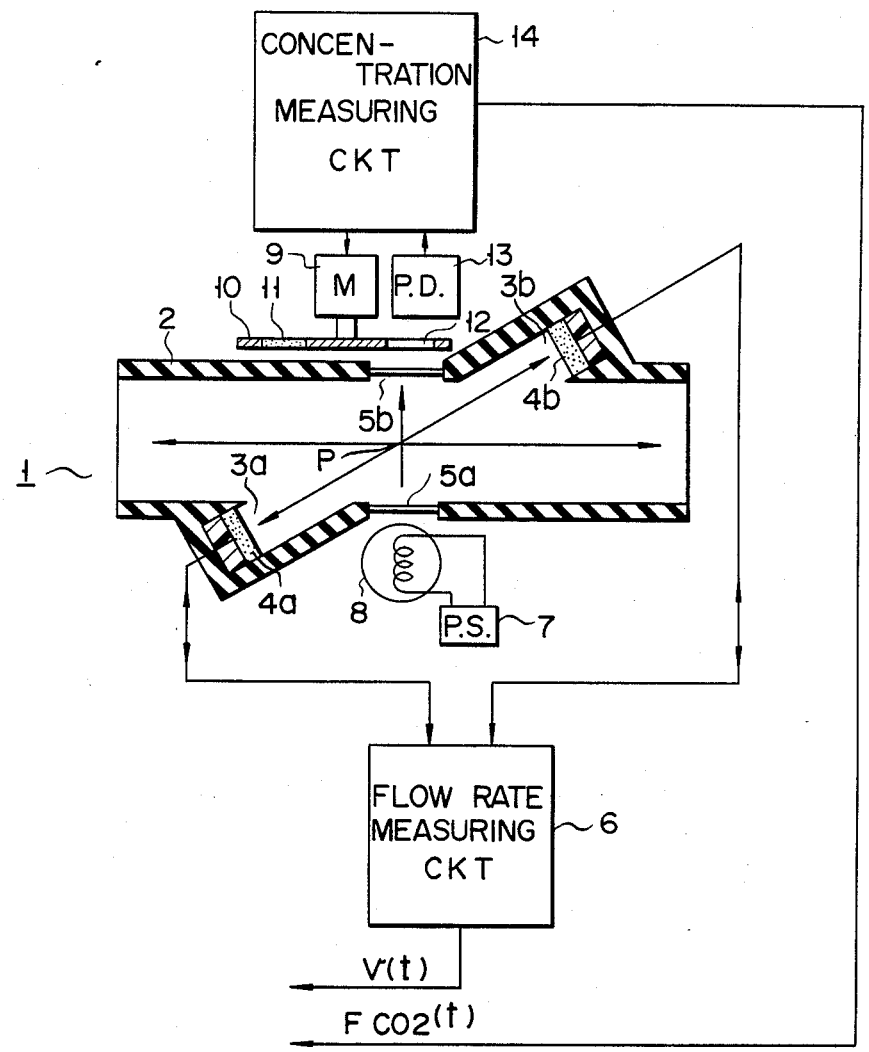
FIG. 1 shows an apparatus for measuring the flow rate and concentration of a fluid which includes a measuring conduit embodying the present invention.

Referring to FIG. 1, a reference numeral 1 denotes a measuring conduit (about 8 cm long) adapted for simultaneously measuring the flow rate and concentration. Ultrasonic transducers for measuring the flow rate and an optical sensor for measuring the concentration are associated with a conduit member 2 through which a fluid to be measured, for example, a respiratory gas, flows. The member 2 has a inner diameter of 13 mm and is made of a chemical-resistant, transparent resin such as a polysulfone, which permits the observation of its inner stains. That is, a pair of ultrasonic transducers 4a and 4b are attached at positions to be separated from each other by a predetermined distance (about 4 cm). They face each other along a slanted line which crosses the flow direction of a fluid flowing through the conduit 2. The ultrasonic transducers 4a and 4b may be provided in the conduit 2 so as to protrude therein; however, in the embodiment, recesses 3a and 3b are formed inside the conduit 2 and the ultrasonic transducers 4a and 4b are arranged so as to have an influence on the flow of the fluid as little as possible.

On the other hand, a pair of light transmitting windows 5a and 5b made of sapphire are airtightly attached to wall of the conduit 2 in a region between the ultrasonic transducers 4a and 4b so as to face each other. These light transmitting windows 5a and 5b are provided to transmit light for measuring the concentration. In the embodiment, the ultrasonic transducers 4a and 4b and the light transmitting windows 5a and 5b are arranged in a manner such that the central light of a light beam passing through the light transitting windows 5a and 5b crosses the cross point P of the central line of the axis of the conduit 2 and the central line of the ultrasonic wave beam which is transmitted and received between the ultrasonic transducers 4a and 4b.

The apparatus for simultaneously measuring the flow rate and the concentration is constituted as follows. A flow measuring circuit 6 is connected to the pair of ultrasonic transducers 4a and 4b. For example, a flow measuring circuit based on a propagation time difference method is used. The measurement of the flow rate by way of the propagation time difference method is disclosed in detail in U.S. Pat. No. 4,425,805.

Figure 2:
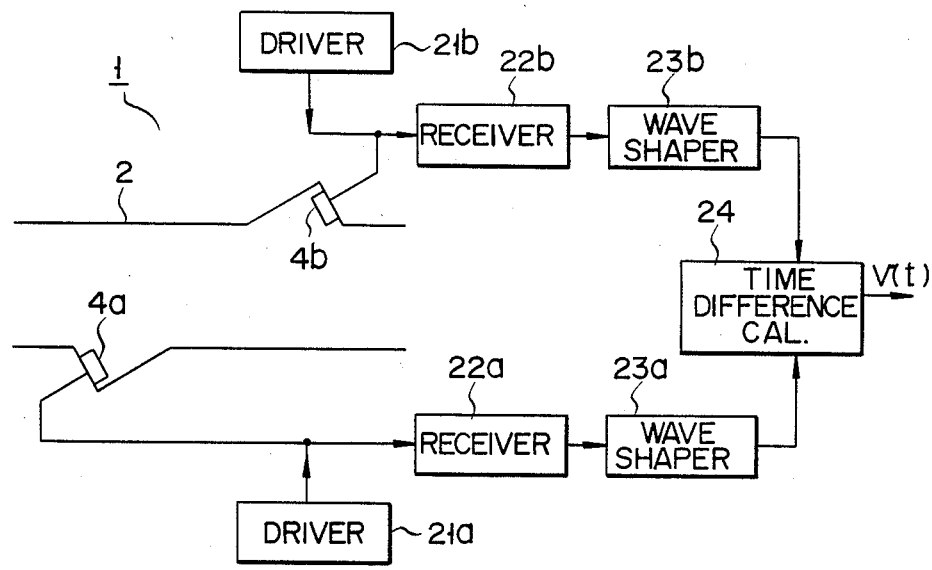
FIG. 2 is a block diagram of a measuring apparatus for measuring the flow rate of a fluid flowing through the conduit.

A basic arrangement of the flow rate measurement based on the propagation time difference method will be described with reference to FIG. 2.

The ultrasonic transducers 4a and 4b are simultaneously driven by burst-like sine wave signals which are generated from drivers 21a and 21b. The ultrasonic waves propagating in the conduit member 2 are received by the other ultrasonic transducers 4b and 4a to be converted to electrical signals. The electrical signals are amplified by receivers 22a and 22b. These signals are sent to a time difference calculating circuit 24 through waveform shaping circuits 23a and 23b, thereby obtaining the propagation time difference between the ultrasonic wave propagating vice versa. By multiplying this difference by a predetermined constant, the flow-rate signal V(t) is derived.

On the other hand, the concentration is measured based on the principle disclosed in, for example, Japanese Laid-Open Patent publication No. 23843/82. That is, a light source 8 which is lit by a power source 7 is provided on the outside of the light transmitting window 5a. The light from the light source 8 is introduced into the conduit 2 through the light transmitting window 5a. The light introduced into the conduit 2 is transmitted through the fluid flowing through the conduit 2, and thereafter it is led to the outside through the other light transitting window 5b. The light introduced to the outside reaches a rotatable chopper 10 which is driven at a constant rotating speed by a motor 9. A first filter 11 and a second filter 12 are arranged in the rotatable chopper 10 at different locations in the circumferential direction. The first filter 11 transmits only the light of a wavelength which is absorbed by a particular component, e.g., carbon dioxide contained in the fluid. The second filter 12 transmits light of which is not absorbed by any components contained in the fluid. The light transmitted through the filters 11 and 12 are introduced to a photo-detector 13 by which they are converted to an electrical signal. Thereafter, the signal is supplied to a component concentration measuring circuit 14.

Figure 3:
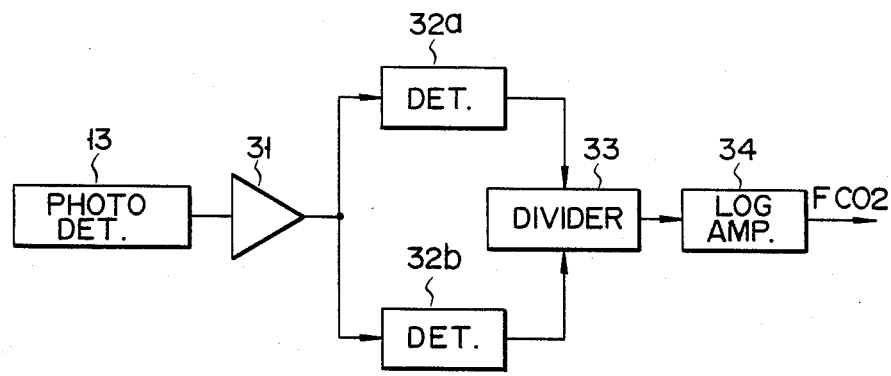
FIG. 3 is a block diagram showing a concentration measuring apparatus for a particular component which is contained in the fluid to be measured.

The concentration measuring circuit 14 is constituted as shown in, for instance, FIG. 3. After a pulse output signal from the photo-detector 13 is amplified by an amplifier 31, it is applied to first and second synchronous detectors 32a and 32b. The peak value of the pulse signal indicating the light amount transmitted through the first filter 11 and the peak value of the pulse signal representing the light amount transmitted through the second filter 12 are respectively detected by the synchronous detectors 32a and 32b synchronously with the rotation of the rotatable chopper 10. The ratio between the peak values of the pulse signals detected by the detectors 32a and 32b is calculated by a divider 33. Further, an output signal from the divider is amplified by a logarithm amplifier 34, thereby obtaining a signal $F_{CO_2}(t)$ which indicates the concentration of a particular component, e.g., carbon dioxide.

In this way, the flow rate signal v(t) and the concentration signal $F_{CO_2}(t)$ are simultaneously derived from the flow measuring circuit 6 and the component concentration measuring circuit 14, respectively.

As described above, according to the present invention, the flow rate and the concentration of a particular component can be simultaneously measured by the same measuring conduit, so that the dead space of the overall measuring system to the fluid can be made smaller than when individual measuring conduits are coupled in tandem. Thus, the burden for a patient is largely reduced. This provides a great advantage in performing a respiration control for a serious patient.

In addition, since the measurements of the flow rate and the concentration of a component are performed by the same measuring conduit, these measuring points are close, so that the time difference in both measurements remarkably reduces. Consequently, there is an advantage such that the signal processing for measurement is simplified. In particular, in the foregoing embodiment, the flow measuring point and the component concentration measuring point concide with each other at the cross point of the central line of the axis of the conduit member and the central line of the ultrasonic beam which is transmitted and received between the pair of ultrasonic transducers, so that this time difference becomes substantially zero. Therefore, it is not necessary at all to perform a processing of the correction for such time difference.

It is not always necessary that the flow measuring point and the component concentration measuring point accurately coincide. An almost similar effect will be obtained even if the cross point of the central line of the axis of the conduit and the central line of the ultrasonic beam transmitted and received between the ultrasonic transducers crosses a part of the light beam which transmits through the light transmitting windows.

Further, in the above embodiment, the plane defined by the central line of the conduit member 2 and the central line of the ultrasonic beam substantially coincides with the plane defined by the central line of the light beam and the central light of the conduit member 2. In other words, the ultrasonic transducers 4a and 4b and the light transmitting windows 5a and 5b are located on a plane on which the central line of the conduit member 2 extends. Therefore, by disposing the measuring conduit 1 so that this plane is set horizontally, even in the case when the fluid flowing through the conduit member 2 is a gas such as a respiratory gas and where such a gas is liquefied in the conduit 2 and the resulting liquid remains in the bottom portion, neither the ultrasonic wave nor the light transmitting the windows 5a and 5b is not blocked by the liquid. Thus, the propagation of the ultrasonic wave and the transmission of the light are not adversely affected, and the measurement can be stably executed.

Figure 4:
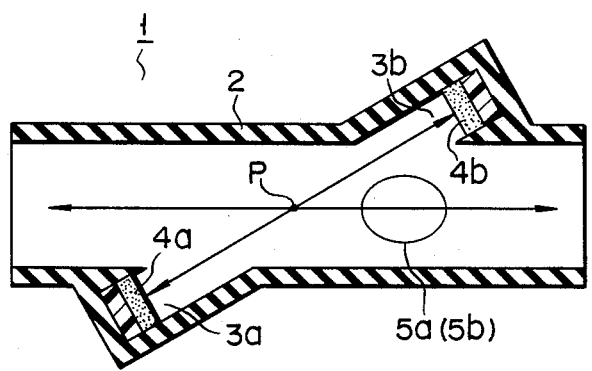
FIG. 4 illustrates a modified form of the measuring conduit of the invention.

FIG. 4 shows an another arrangement of a measuring condition of the invention. In this embodiment, the light beam which transmits through the light transitting windows 5a and 5b does not cross the cross point of the central line of the conduit 2 and the central line of the ultrasonic beam transmitted and received between the ultrasonic transducers 4a and 4b; however, the light transmitting windows 5a and 5b are attached in the wall of the conduit 2 in the region between the ultrasonic transducers 4a and 4b. With such an arrangement, in the case when the axial length of the conduit 2 between the ultrasonic transducers 4a and 4b is short (about a few centimeters), the time difference between the flow measurement and the concentration measurement will not raise any problem. Even if this time difference is compensated, a change in time difference due to a change in flow velocity can be ignored. Thus, there is an advantage such that a signal processing for correction is remarkably simplified.

What is claimed is:

1. A measuring conduit adapted for measuring flow rate and concentration of a fluid for use in a measuring apparatus arranged to measure both the flow rate of the fluid containing a particular gas component using an ultrasonic wave and the concentration of the particular gas component in an optical manner, comprising:
   a single conduit member through which said fluid flows;
   a pair of ultrasonic transducers attached to said conduit member so as to face each other along a line slanted with respect to a flow direction of the fluid for measuring the flow rate of the fluid; and
   a pair of light transmitting windows airtightly provided in the wall of said conduit member between said ultrasonic transducers so as to face each other, one of said light transmitting windows introducing a light which is emitted from an external light source into said conduit member, and the other light transmitting window introducing the light penetrating the fluid flowing through said conduit member into a photo detecting element in said measuring apparatus.

2. A measuring conduit according to claim 1, wherein said ultrasonic transducers and said light transmitting windows are arranged so that a cross point of the central line of said conduit member and the central line of the ultrasonic beam transmitted and received between said ultrasonic transducers coincides with the central line of the light beam transmitted through said light transmitting windows.

3. A measuring conduit according to claim 1, wherein said ultrasonic transducers and said light transmitting windows are arranged so that a cross point of the central line of said conduit member and the central line of the ultrasonic beam transmitted and received between said ultrasonic transducers crosses a part of the light beam passing through said light transmitting windows.

4. A measuring conduit according to claim 1, wherein said ultrasonic transducers and said light transmitting windows are arranged so that a plane defined by the central line of said conduit member and the central line of the ultrasonic beam transmitted and received between said ultrasonic transducers substantially coincides with a plane defined by the central line of said conduit member and the central line of the light beam passing through said light transmitting windows.

* * * * *